(12) United States Patent
Press

(10) Patent No.: US 9,427,034 B1
(45) Date of Patent: Aug. 30, 2016

(54) HAND SACK SYSTEM AND METHOD

(71) Applicant: Roberta Press, Del Ray Beach, FL (US)

(72) Inventor: Roberta Press, Del Ray Beach, FL (US)

(*) Notice: Subject to any disclaimer, the term of this patent is extended or adjusted under 35 U.S.C. 154(b) by 5 days.

(21) Appl. No.: 14/974,666

(22) Filed: Dec. 18, 2015

Related U.S. Application Data

(63) Continuation-in-part of application No. 14/628,739, filed on Feb. 23, 2015, now Pat. No. 9,326,881.

(51) Int. Cl.
*A41D 19/00* (2006.01)
*A61F 7/00* (2006.01)
*A41D 19/01* (2006.01)
*A41D 19/015* (2006.01)

(52) U.S. Cl.
CPC .............. *A41D 19/01* (2013.01); *A41D 19/001* (2013.01); *A41D 19/0006* (2013.01); *A41D 19/0017* (2013.01); *A41D 19/01529* (2013.01); *A61F 2007/0036* (2013.01)

(58) Field of Classification Search
CPC .............. A41D 19/00; A41D 19/0006; A41D 19/0013; A41D 19/0017; A41D 19/0065; A41D 19/01529; A41D 19/01535; A41D 19/01541; A41D 19/15; A61F 2007/0036; A61F 5/013
USPC ..................................... 2/158, 159, 164, 247
See application file for complete search history.

(56) References Cited

U.S. PATENT DOCUMENTS

| | | | | |
|---|---|---|---|---|
| 5,020,161 A * | 6/1991 | Lewis, Jr. | ........ | A41D 19/01529 2/159 |
| 5,050,596 A * | 9/1991 | Walasek | ............ | A41D 19/0068 2/158 |
| 5,437,621 A * | 8/1995 | Andrews | ............... | A61F 13/104 2/16 |
| 5,444,874 A * | 8/1995 | Samelian | ........... | A41D 19/0013 2/159 |
| 5,740,551 A * | 4/1998 | Walker | ............... | A41D 19/0006 2/16 |
| 5,869,072 A * | 2/1999 | Berry | ..................... | A41D 19/00 2/159 |
| 7,644,448 B2 * | 1/2010 | Grilliot | ............. | A41D 19/0013 2/161.6 |
| 2010/0217362 A1* | 8/2010 | Parsons | ................ | A41D 19/002 607/111 |
| 2013/0066409 A1* | 3/2013 | Hilton | .................. | A01K 13/006 607/110 |
| 2015/0173429 A1* | 6/2015 | Williams | ......... | A41D 19/01529 2/160 |

* cited by examiner

Primary Examiner — Kari Petrik

(57) ABSTRACT

A glove has a finger section receiving the fingers, an intermediate section receiving the palm, and a wrist section receiving the wrist of a person. The glove has a front, a back, and sides. An inner layer of fluid retaining cotton material is provided to be worn in direct contact with the fingers and the palm. A middle layer of moisture barrier material is provided in contact with the inner layer. An outer layer of stretchable material is provided in contact with the middle layer and the wrist. A slit extends in the front through the outer layer and the middle layer. Fluid moistens the inner layer prior to wearing by passage through the slit.

2 Claims, 3 Drawing Sheets

HAND SACK SYSTEM AND METHOD

RELATED APPLICATION

The present application is a continuation-in-part of pending application Ser. No. 14/628,739, filed Feb. 23, 2015, the subject matter of which is incorporated herein by reference.

FIELD OF THE INVENTION

The present invention relates to a hand sack system and method and more particularly pertains to relieving pain. The relieving of pain is done in a safe, convenient, and economical manner.

DESCRIPTION OF THE PRIOR ART

The use of therapeutic hand sack systems and methods of known designs and configurations is known in the prior art. More specifically, therapeutic hand sack systems and methods of known designs and configurations previously devised and utilized for the purpose of relieving pain are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, they do not describe a hand sack system and method that allows for the relieving of pain in a safe, convenient, and economical manner.

In this respect, the hand sack system and method according to the present invention substantially departs from the conventional concepts and designs of the prior art, and in doing so provides an apparatus primarily developed for the purpose of relieving pain is done in a safe, convenient, and economical manner.

Therefore, it can be appreciated that there exists a continuing need for a new and improved hand sack system and method which can be used for relieving pain in a safe, convenient, and economical manner. In this regard, the present invention substantially fulfills this need.

SUMMARY OF THE INVENTION

In view of the disadvantages inherent in the known types of therapeutic hand sack systems and methods of known designs and configurations now present in the prior art, the present invention provides an improved hand sack system and method. As such, the general purpose of the present invention, which will be described subsequently in greater detail, is to provide a new and improved hand sack system and method which has all the advantages of the prior art and none of the disadvantages.

To attain this, the present invention essentially comprises a glove which has a finger section receiving the fingers, an intermediate section receiving the palm, and a wrist section receiving the wrist. An inner layer of fluid retaining cotton material is provided to be worn in direct contact with the fingers and the palm. A middle layer of moisture barrier material is provided in contact with the inner layer. An outer layer of stretchable material is provided in contact with the Middle layer and the wrist. A slit extends through the cuter layer and the middle layer. Fluid moistens the inner layer by passage through the slit.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilised as a basis for the designing of other structures, methods, and systems for carrying out the several purposes of the present invention. It is important, therefore, that the claims be regarded as including such equivalent constructions insofar as they do not depart from the spirit and scope of the present invention.

It is therefore an object of the present invention to provide a new and improved hand sack system and method which has all of the advantages of the prior art therapeutic hand sack systems and methods of known designs and configurations and none of the disadvantages.

It is another object of the present invention to provide a new and improved hand sack system and method which may be easily and efficiently manufactured and marketed.

It is further object of the present invention to provide a new and improved hand sack system and method which is of durable and reliable constructions.

An even further object of the present invention is to provide a new and improved hand sack system and method which is susceptible of a low cost of manufacture with regard to both materials and labor, and which accordingly is then susceptible of low prices of sale to the consuming public, thereby making such hand sack system and method economically available to the buying Public.

Lastly, even still another object of the present invention is to provide a hand sack system and method for relieving pain. The relieving of pain is done in a safe, convenient, and economical manner.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
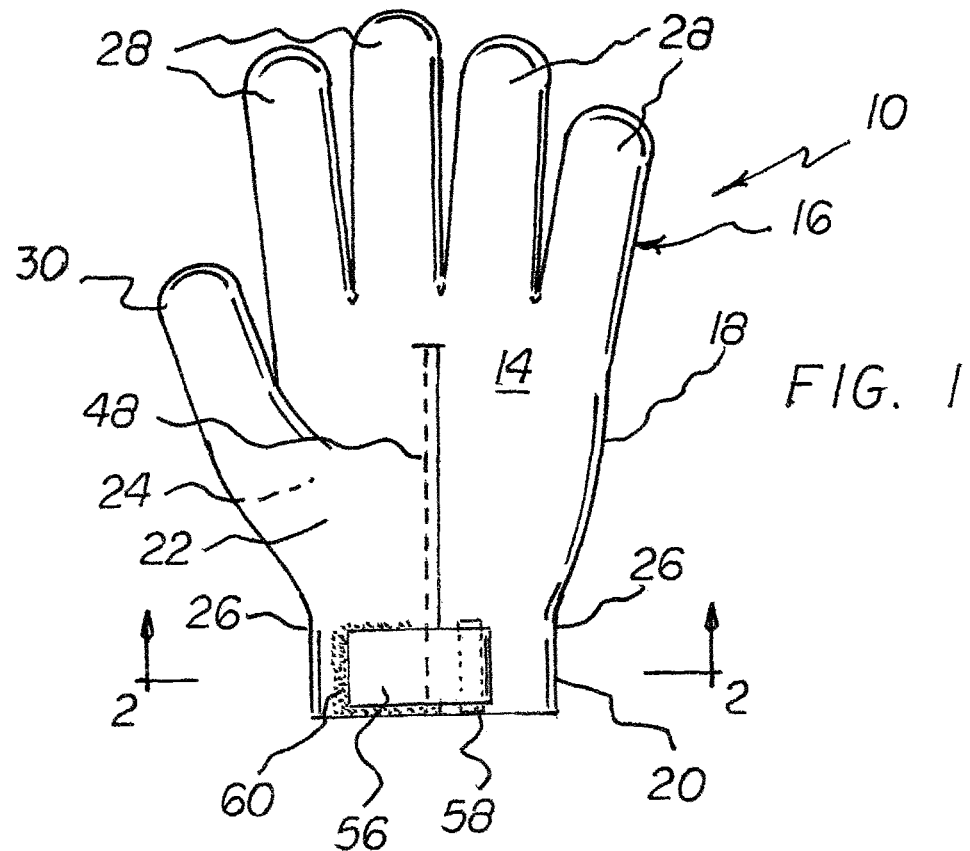
FIG. 1 is a front elevational view of a hand sack system constructed in accordance with the principles of the present invention.
Figure 2:
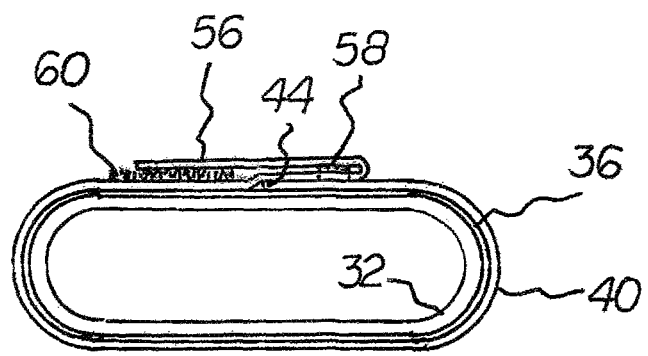
FIG. 2 is a cross sectional view taken along line 2-2 of FIG. 1.
Figure 3:
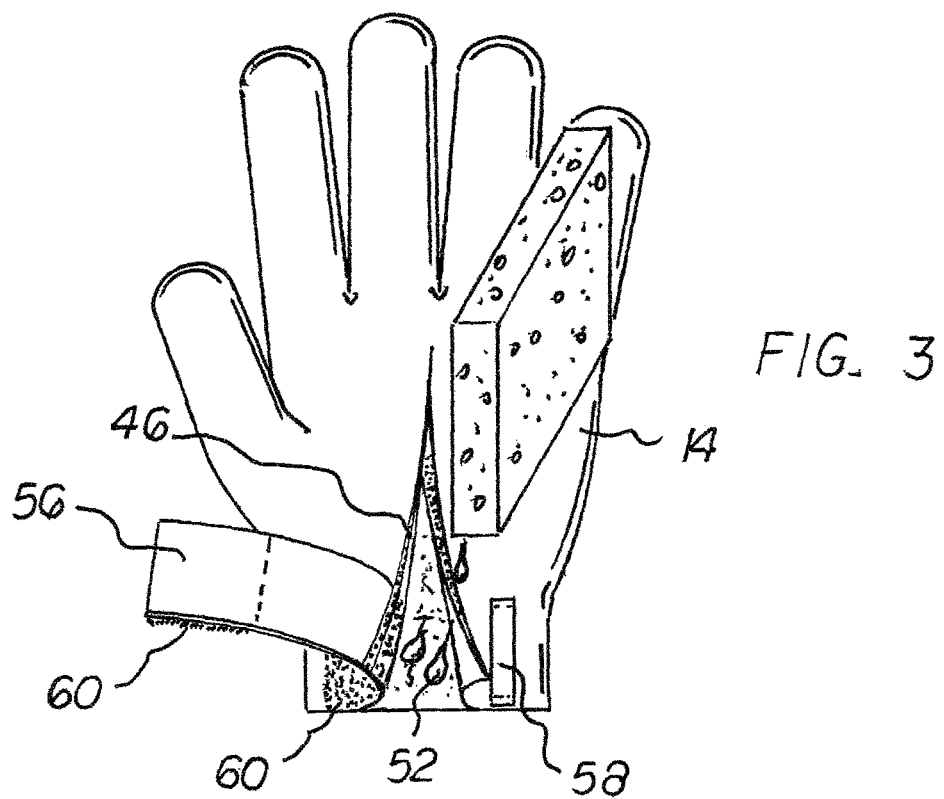
FIG. 3 is a perspective illustration of the hand sack system shown in FIGS. 1 and 2 with the slit opened and the inner layer being moistened.

With reference now to the drawings, and in particular to FIG. 1 thereof, the preferred embodiment of the new and improved hand sack system and method embodying the principles and concepts of the present invention and generally designated by the reference numeral 10 will be described.

The present invention, the hand sack system 10 is comprised of a plurality of components. Such components in their broadest context include a glove, an inner layer, a middle layer, and outer layer, a slit and fluid. Such components are individually configured and correlated with respect to each other so as to attain the desired objective.

The hand sack system 10 is for relieving pain. The relieving is done in a safe, convenient, and economical manner.

First provided is a glove 14. The glove is for a person with a hand. The hand has fingers, a palm, and a wrist. The glove having a finger section 16, an intermediate section 18 and a wrist section 20. The glove has a front 22, a back 24, and sides 26. The glove is adapted to be worn on the hand of the person. The finger section is formed of four finger components 28 and a thumb component 30.

An inner layer 32 of fluid retaining cotton material is provided. The inner layer is to be worn in direct contact with the fingers and the palm. The inner layer has a thickness essentially equal to the thickness of a conventional T-shirt. The inner layer is adapted to be moistened with fluid through the slit by way of a clean sponge prior to being worn by the person.

Next, a middle layer 36 of moisture barrier plastic material is provided. The middle layer is in contact with the inner layer.

Next, an outer layer 40 of stretchable material is provided. The outer layer is in contact with the middle layer and the wrist.

A slit 44 is next provided. The slit extends through the outer layer and the middle layer. The slit is located on the intermediate section through the front. Hook and loop fasteners 46 are provided and are adapted to open and close the slit. Elastic threads 48 extend around the slit through the inner layer and middle layer and outer layer.

Fluid 52 is next provided. The fluid is adapted to moisten the inner layer by adding the fluid through the slit by way of a clean sponge prior to putting on the hand sack system. The preferred fluid to be used for contacting the skin of the user is water, hot or very warm water or, in the alternative, very cold or ice water.

With the cotton inner layer moistened, the glove is placed on the hand of the person with the inner layer in contact with the fingers and the palm and with the middle layer in contact with the inner layer and with the outer layer in contact with the middle layer and the wrist.

Finally, an elastic securement strap 56 is provided. The securement strap extends from the slit at the wrist section. A turnaround keeper 58 is provided for the passage of the elastic securement strap. The lower edge of the glove extends essentially one in below the wrist of the wearer. Supplemental hook and loop fasteners 60 adjustably couple the elastic securement strap to the wrist section.

Figure 4:
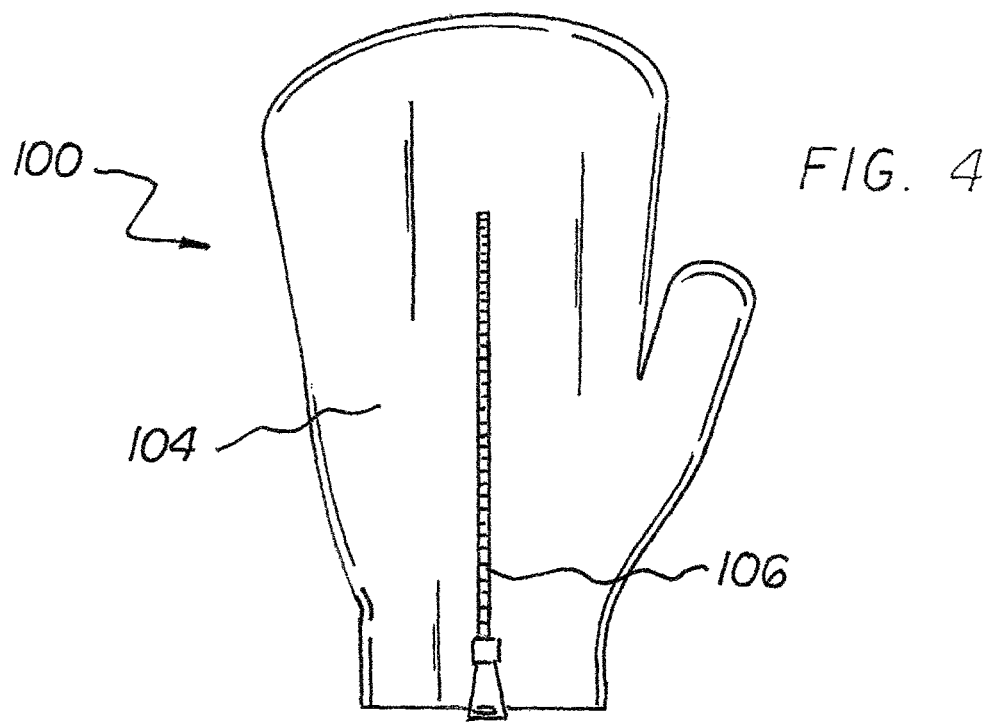
FIG. 4 is a rear elevational view of a hand sack system constructed in accordance with an alternate embodiment of the present invention.

An alternate embodiment of the invention is shown in FIG. 4. In this embodiment of the system 100, the glove is a mitten which includes a single finger component and a thumb component. The slit is in the front 104 in this embodiment. Also included is a sliding fastener 106 for holding the slit closed.

Figure 5:
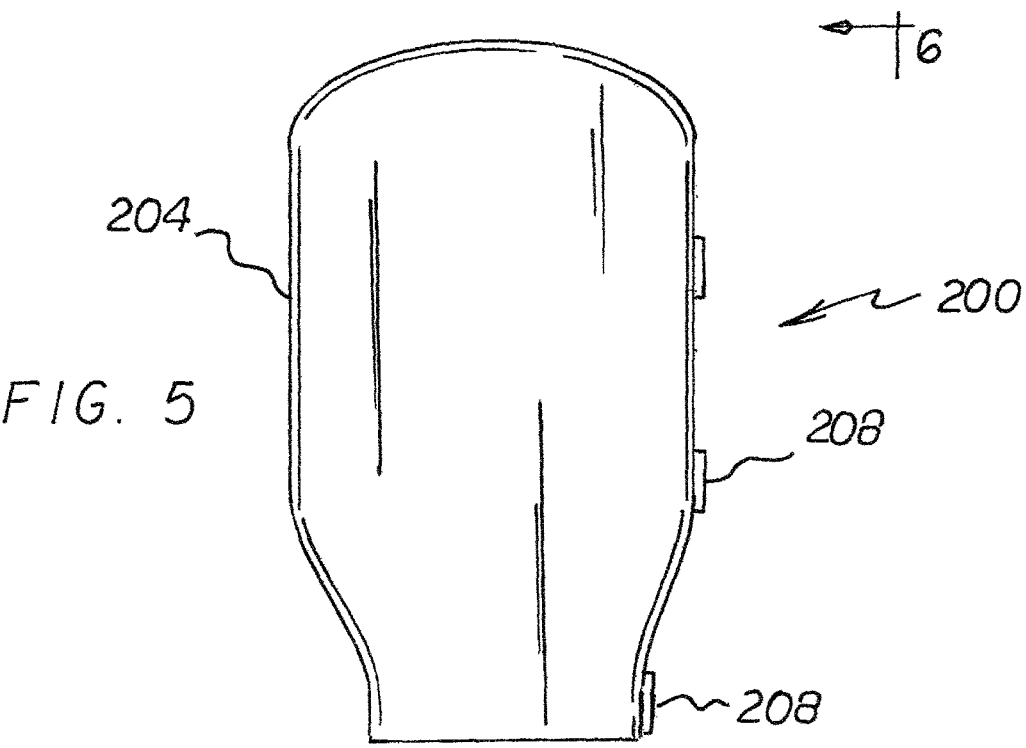
FIG. 5 is a front elevational view of a hand sack system constructed in accordance with another alternate embodiment of the present invention.
Figure 6:
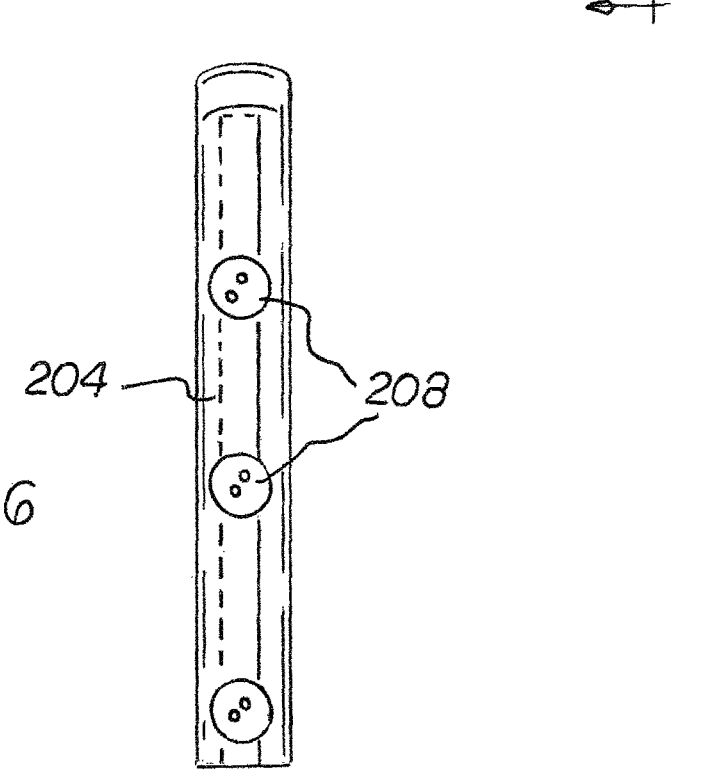
FIG. 6 is a side elevational view taken along line 6-6 of FIG. 5.

Reference is now made to the embodiment shown in FIGS. 5 and 6. In this embodiment of the system 200, the glove is a hand-sack which includes one component for the fingers and the thumb. In this embodiment, the slit is in the front. Further included are buttons or snaps 208 for holding the slit closed.

This hand-sack embodiment is preferably constructed slightly larger than the prior embodiments. In this manner pressure to painful hands with attendant pain is minimized.

In all embodiments, the wrist section extends downwardly for 1 inch below the wrist. Further, for best results, the system should be used at bedtime, never outdoors, for at least 4 hours, the longer, the better.

The invention also includes a method of wearing the hand sack to relieve pain. The first step of the preferred method is providing a glove 14 for a person with a hand having fingers, a palm, and a wrist. The glove has a finger section 16, an intermediate section 18, and a wrist section 20. The glove has a front 22, a back 24, and sides 26. The glove is adapted to be worn on the hand of the person. The finger section is formed of four finger components 28 and a thumb component 30.

The next step is providing an inner layer 32 of fluid retaining cotton material to be worn in direct contact with the fingers and the palm. The inner layer has a thickness essentially equal the thickness of a commercially available T-shirt. The inner layer is adapted to be moistened with fluid added by a clean sponge prior to being worn by the person.

The next step is providing a middle layer 36 of moisture barrier plastic material. The middle layer is in contact with the inner layer.

The next step is providing an outer layer 40 of stretchable material. The outer layer is in contact with the middle layer and the wrist.

The next step is forming a slit 44 extending through the outer layer and the middle layer. The slit is located on the intermediate section through the front. Hook and to fasteners 46 are adapted to open and close the slit. Elastic threads 48 extend around the slit through the inner layer and middle layer and outer layer.

The next step is moistening the inner layer by pouring fluid through the slit.

The next step is placing the glove on the hand of the person with the inner layer contacting the fingers and the palm with the middle layer contacting the inner layer and with the outer layer in contact with the middle layer and the wrist.

The final step is providing an elastic securement strap extending from the slit at the wrist section, a turnaround keeper for the passage of the elastic securement strap, and supplemental hook and loop fasteners adjustably coupling the elastic securement strap to the wrist section, the glove ending one inch below the wrist of the user.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A method of wearing a hand sack for relieving pain, the method including the steps of:
    providing a glove (14) for a person with a hand, the hand having fingers, a palm, and a wrist, the glove having a finger section (16), an intermediate section (18) and a wrist section (20), the glove having a front (22) and a back (24) and sides (26), the glove adapted to be worn on the hand of the person, the finger section being formed of four finger components (28) and a thumb component (30);
    wherein the glove comprises an inner layer (32) of fluid retaining cotton material to be worn in direct contact with the fingers and the palm, the inner layer having a thickness, the inner layer adapted to be moistened with fluid prior to being worn by the person;
    wherein the glove comprises a middle layer (36) of moisture barrier plastic material in contact with the inner layer;
    wherein the glove comprises an outer layer (40) of stretchable material in contact with the middle layer and the wrist;
    wherein the glove comprises a slit (44) extending through the outer layer and the middle layer, the slit located on the intermediate section through the front of the glove;
    wherein the glove comprises hook and loop fasteners (46) adapted to open and close the slit;
    wherein the glove comprises elastic threads (48) extending around the slit through the inner layer and middle layer and outer layer;
    moistening the inner layer by adding fluid through the slit by way of a clean sponge; and
    placing the glove on the hand of the person with the inner layer in contact with the fingers and the palm, and with the middle layer in contact with the inner layer, and with the outer layer in contact with the middle layer and the wrist.

2. The method as set forth in claim 1 wherein the fluid to be used for contacting skin of the user is water.

* * * * *